United States Patent [19]

Ishikawa et al.

[11] Patent Number: 4,730,494

[45] Date of Patent: Mar. 15, 1988

[54] METHOD FOR EXAMINING A SURFACE OF A SAMPLE BY MEANS OF ULTRASOUND

[75] Inventors: Isao Ishikawa, Hino; Hiroshi Kanda, Tokorozawa; Kageyoshi Katakura, Tokyo, all of Japan

[73] Assignee: Hitachi, Ltd., Tokyo, Japan

[21] Appl. No.: 904,400

[22] Filed: Sep. 8, 1986

[30] Foreign Application Priority Data

Oct. 7, 1985 [JP] Japan ................... 60-221806

[51] Int. Cl.⁴ ........................................... G01N 29/04
[52] U.S. Cl. ...................................................... 73/606
[58] Field of Search ........................ 73/606, 627, 629

[56] References Cited

U.S. PATENT DOCUMENTS 4,541,281  9/1985  Chubachi et al. .................. 73/606
4,603,585  8/1986  Atalar ................................. 73/606

OTHER PUBLICATIONS

Curtis, G. J., "The Use of Surface Elastic Waves in Examining Surface Mechanical Properties." In: Szilard, J., *Ultrasonic Testing* (New York, Wiley, 1982), pp. 302–303. TA 417.4.U4.
Atalar, A. et al., "Phase Imaging in Reflection with the Acoustic Microscope." *Applied Physics Letters*, vol. 31, No. 12 (Dec. 15, 1977), pp. 791–793.

*Primary Examiner*—John Chapman
*Attorney, Agent, or Firm*—Antonelli, Terry & Wands

[57] ABSTRACT

A method for examining a layer having defects and in particular the thickness of a machining damaged layer on a surface of a sample by means of a focused ultrasound beam and a device for realizing the method are disclosed, in which a focused ultrasound beam is generated and ultrasound reflected by the sample is detected. Curves (called V(z) curves) representing the relation of the distance between a transducer detecting the reflected ultrasound and the sample versus the detection output are traced while varying the distance and this measurement is repeated while varying the frequency of the focused ultrasound beam. The propagation velocity of surface acoustic wave in the sample is calculated on the basis of the period in each of the plurality of V(z) curves and a frequency dependence characteristic curve for the propagation velocity is obtained. The thickness of the machining damaged layer in the surface portion of the sample is evaluated from inflection points in the frequency dependence characteristic curve.

4 Claims, 4 Drawing Figures

METHOD FOR EXAMINING A SURFACE OF A SAMPLE BY MEANS OF ULTRASOUND

BACKGROUND OF THE INVENTION

This invention relates to a method for examining a surface of a sample, the state near the surface, and in particular the thickness of its machining damaged layer by means of a focused ultrasound beam and to a device for realizing the method.

Recently it has become possible to generate and detect sonic waves of ultra high frequency up to 1 GHz and thus to realize a sonic wavelength of about 1 μm in water. As the result, it is disclosed in U.S. Pat. No. 4,028,933 to be able to obtain an ultrasound imaging apparatus having a high resolving power. That is, a high resolving power up to 1 μm can be realized by forming a focused ultrasound beam by means of a concave lens.

By inserting a sample to be studied in the beam, detecting ultrasound reflected by the sample, and displaying the intensity of signals obtained while moving mechanically the sample two-dimensionally on the screen of a cathode ray tube by using them as the brightness signal, it is possible to observe the microstructure of the sample in an enlarged scale.

Further it is desclosed in Appl. Phys. Lett. 31 (12), Dec. 15, 1977, pp. 791-793 that elastic characteristics, the presence of scratches, etc. on the surface of the sample can be known by means of such a focused ultrasound beam. According to this article, characteristics of the surface of the sample can be estimated on the basis of a curve (called V(z) curve) obtained by plotting the intensity of reflected ultrasound, detected while varying the distance between the sample and the lens.

On the other hand, it is desired to establish a method for evaluating damages in very fragile materials such as ceramics, because the strength of such materials depends strongly on defects existing within the materials or on micro defects produced in the surface portion of the sample during machining.

However it has been considered that it is difficult to evaluate the degree of the defects causing deterioration in strength, i.e. the thickness of the machining damaged layer with a high efficiency in a nondestructive manner.

SUMMARY OF THE INVENTION

An object of this invention is to provide a new examination method and a device therefor, by which the above described examination method using a V(z) curve is further developed.

Another object of this invention is to provide an examination method permitting to know the thickness of a machining damaged layer of the sample and a device for realizing it.

By the examination method according to this invention:

the sample is irradiated through a liquid medium with a focused ultrasound beam;

curves representing variations of detection out with respect to variations of the distance between the sample and the source of the focused ultrasound beam (called V(z) curves) are obtained by detecting ultrasound reflected by the sample while varying the distance;

the propagation velocity of surface acoustic wave in the sample is measured on the basis of the period of the V(z) curves;

this measurement is repeated while varying the frequency of the focused ultrasound beam and a frequency dependence curve of the propagation velocity is obtained; and the thickness of the layer having surface defects in the sample is obtained on the basis of the frequency dependence curve of the propagation velocity.

That is, the ultrasound beam entering the sample from the liquid medium with the critical angle excites surface acoustic wave in the surface portion of the sample. The V(z) curves stated above indicate the state of interference between ultrasonic wave reemitted by the sample after propagation in the form of surface acoustic wave in the surface portion of the sample and ultrasonic wave reflected directly by the surface of the sample. The period $\Delta Z$ in these V(z) curves depends on the propagation velocity $V_R$ of the surface acoustic wave, the velocity $V_w$ of the ultrasound in the liquid medium and the wavelength $\lambda_w$ in the liquid medium and can be represented by the following equation:

$$\Delta Z = (V_R/V_W)^2 \lambda_w \qquad (1)$$

Consequently, the value of $V_R$ can be determined by using $\Delta Z$, $V_W$ and $\lambda_W$.

This invention is characterized specifically in that the measurement described above is effected while varying the frequency of the ultrasound and that the thickness of the machining damaged layer is examined on the basis of the frequency dependence characteristics of $V_R$ obtained in this way. That is, since the propagation domain of the surface acoustic wave in the sample is shallower with increasing frequency, the region where micro cracks, plastic strains, etc. influencing the propagation velocity exist, i.e. the thickness of the machining damaged layer can be calculated by using inflection points in the frequency characteristic curve of the propagation velocity of the surface acoustic wave.

DESCRIPTION OF THE PREFERRED EMBODIMENTS

Figure 1:
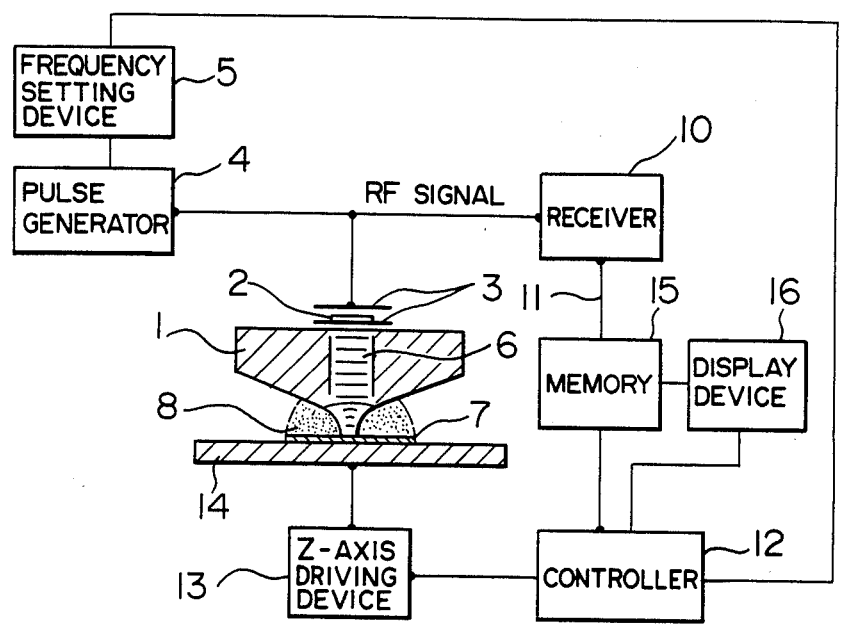
FIG. 1 is a block diagram indicating the construction of an embodiment of devices for realizing the examination method according to this invention.

FIG. 1 indicates an embodiment of devices for realizing the examination method according to this invention. A focused ultrasound beam is generated by a spherical lens 1, a piezo-electric film 2 and a pair of electrodes 3, which constitute also an ultrasonic transducer detecting reflected ultrasound. This structure can be constructed by obtaining the spherical lens 1 by forming a semispherical recess having a 0.1 mm to 1.0 mm at an end of a cylindrical body made of molten quartz and on the other hand by polishing the other end in the optical grade and disposing the piezo-electric film 2 made of ZnO, etc. interposed between a pair of electrodes 3 in the form of a sandwich thereon. The space between this semispherical recess and the sample is filled with a medium 8 (e.g. water) for propagating ultrasonic wave 6 to the sample 7.

The ultrasonic wave 6 generated by driving the piezo-electric film 2 by means of a pulse generator 4 propagates as a plane wave in the cylindrical body. When this plane wave reaches the semispherical recess, a refracting action is produced due to a difference between the sound velocities in quartz (sound velocity 6000 m/s) and in water (sound velocity 1500 m/s) and thus a focused ultrasound beam 6 is projected on a surface of the sample 7. To the contrary, ultrasound reflected by the sample 7 is focused and phased by the spherical lens, reaches the piezo-electric film 2, and is transformed there into an RF signal. This RF signal is received by a receiver 10, where it is detected by means of a diode and transformed into detection signal 11 in the video frequency band.

On the other hand, the sample 7 is located on a sample holder 14, which is driven in the vertical direction by a Z-axis driving device. In this way the distance between the sample 7 and the spherical lens 1 can be varied at very small intervals, while the frequency of the RF signal repeatedly produced in the form of bursts by a pulse oscillator 4 is determined by a frequency setting device 5. The frequency setting device 5 and the Z-axis driving device 13 are controlled by a controller 12. In this way the frequency and the distance between the lens and the sample are varied successively in the order stated later and every time a detection signal of the reflected ultrasound is obtained.

The detection signal repeatedly obtained is stored in a memory 15. The stored signal is successively read-out under the control of the controller 12 and a curve (V(z) curve) is displayed on a display device 16, in which the abscissa represents the displacement along the Z-axis (in the vertical direction) of the sample and the ordinate the intensity of the detection signal. An X-Y plotter, a CRT display device, etc. can be used as the display device 16.

Figure 2:
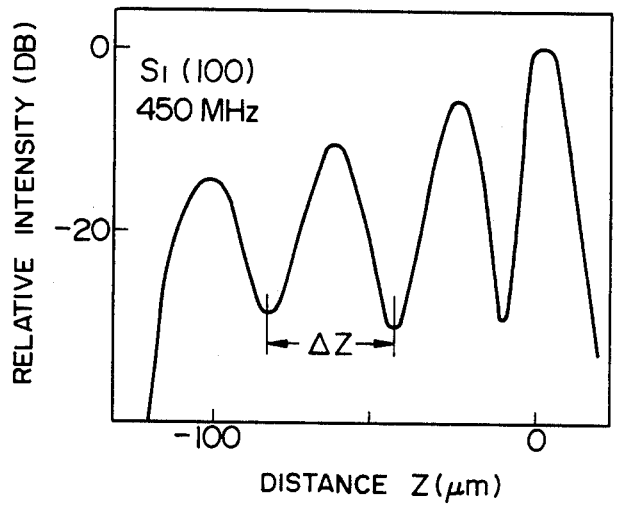
FIG. 2 is a graph illustrating an example of V(z) curves.

There are two methods for controlling successively the frequency and the distance between the sample and the lens by means of the controller 12. According to the first method the frequency is fixed and the measurement is repeated while displacing the sample holder 14 in the Z direction. In this way the V(z) curve obtained on the display device 16 is e.g. as indicated in FIG. 2. FIG. 2 shows a V(z) curve representing the intensity of reflected signal obtained by irradiating a (100) surface of silicon with a focused ultrasound beam having a frequency of 450 MHz, in which the abscissa represents the relative intensity of reflected signal and the ordinate the distance between the sample and the lens, and 0 in the scale of the abscissa corresponds to the distance, for which the focal point of the focused ultrasound beam is just in agreement with the surface of the sample. This measurement for obtaining the V(z) curve in such a manner while varying the distance between the sample and the lens is repeated while varying the frequency.

According to the second method the sample holder 14 is fixed and a measurement is effected while varying the frequency of the RF signal, i.e. the frequency of the projected focused ultrasound beam in a predetermined range . Then another measurement is effected in the same way while varying the frequency, after having displaced slightly the sample holder 14. After that, the same measurement is repeated successively while displacing slightly the sample holder 14 successively.

By either method data on the intensity of the reflected signal obtained by the repeated measurements are stored in the memory 15. In this way a plurality of V(z) curves are obtained for various frequencies.

Unevenness of the V(z) curves depends on variations of the path length of the surface acoustic wave in the surface portion of the sample produced by variations of the distance between the sample and the lens and it is produced by interference between the reflected wave in which this surface acoustic wave is interposed and the wave reflected directly by the surface of the sample. Its period $\Delta Z$ (refer to FIG. 2) can be represented by Eq. (1) stated previously and therefore the propagation velocity $V_R$ of the surface acoustic wave in the sample can be given by $$V_R = V_W \sqrt{\frac{\Delta Z}{\lambda_W}} \tag{2}$$

Figure 3:
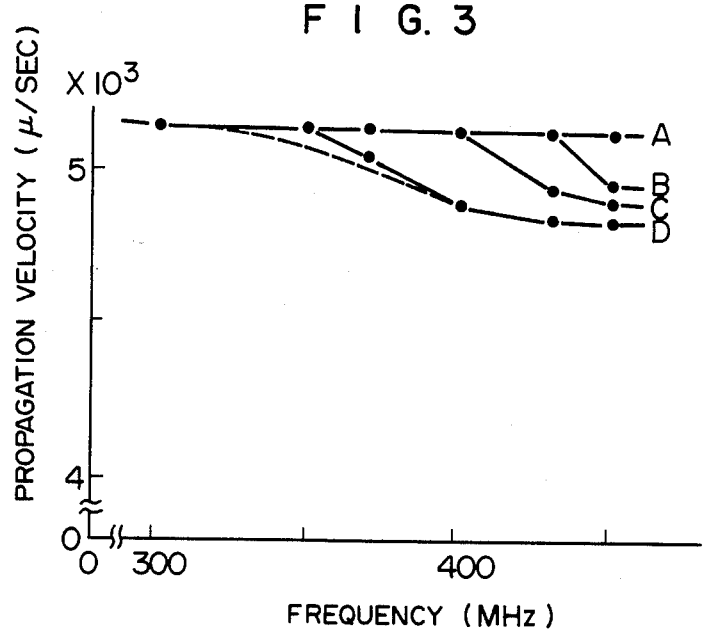
FIG. 3 is a graph illustrating some examples of frequency dependence curves of the propagation velocity, which can be obtained according to this invention.

FIG. 3 indicates measurement results obtained by measuring the propagation velocity of the surface acoustic wave for a plurality of samples, whose surfaces are polished under various working conditions, according to the method described above, while varying the frequency from 300 MHz to 450 MHz.

The propagation velocities were approximately equal for all the samples under 350 MHz, but they were different for the frequencies higher than it. At a frequency of 450 MHz the propagation velocities for samples B, C and D were reduced by 3, 4 and 5%, respectively, with respect to that for a sample A having no strain. It was also known that the aspect of their variations is closely related to the roughness of their surface.

It is thought that different propagation velocities in different samples at 450 MHz are a result of the fact that the domain through which the surface acoustic wave propagates becomes shallower with increasing frequency and factors influencing the propagation are located more closely to the surface therewith so that the surface acoustic wave is influenced more strongly by different elastic properties of the surface portion due to micro cracks and plastic strains introduced during machining. Consequently it is possible to evaluate the thickness of the machining damaged layer on the basis of the frequency dependence of the propagation velocity and in particular the frequencies corresponding to inflection points in curves representing it.

Figure 4:
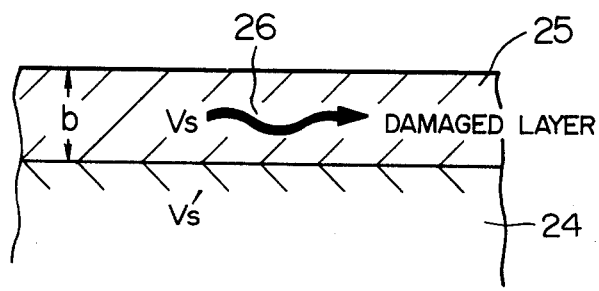
FIG. 4 is a scheme representing the propagation of surface acoustic wave.

The frequency dependence of the propagation velocity of Lamb wave in a stratified structure consisting of a machining damaged layer 25 having a thickness b formed on a silicon substrate 24 having no strain, as indicated in FIG. 4, may be obtained by isotropic approximation. Suppasing that the propagation velocities of the surface acoustic wave 26 for the latter and the former are $V_S$, and $V_S'$, respectively the propagation velocity in a stratified structure can be given in a functional form;

$$V_R = f(V_S, V_S', b, \omega), \tag{3}$$

$\omega$ being the frequency. Consequently, when the low and the high frequency limit are used for $V_S'$ and $V_S$, respectively, studying the accordance of measured values with theoretical values obtained by using b as a parameter, it is possible to obtain the thickness represented by b. The broken line in FIG. 3 indicates a theoretical curve of calculation results, supposing $b = 5.4$ $\mu$m, which shows a relatively good agreement with experimental results of sample D.

Therefore, the thickness of the machining damaged layer of sample D which is produced by #2000 abrasive can be evaluated to be about 5 μm.

As explained above, according to this invention, since the thickness of the machining damaged layer can be measured in a non-destructive manner by measuring the propagation velocity of the surface acoustic wave while varying the frequency of used ultrasound and obtaining inflection points in curves representing variations of the velocity, an important industrial advantage can be obtained.

We claim:

1. Method for examining a surface layer of a stratified structure of a sample by means of ultrasound, comprising:
   a step of irradiating the sample through a liquid medium with a focused ultrasound beam;
   a step of obtaining a curve representing variations of detection output with respect to the distance between said sample and the source of said focused ultrasound beam by detecting ultrasound reflected by said sample while varying the distance;
   a step of measuring the propagation velocity of surface acoustic wave in said sample on the basis of the period in said curve representing variations of detection output;
   a step of obtaining a frequency dependence curve for said propagation velocity by repeating the above measurement while varying the frequency of said focused ultrasound beam; and
   a step of evaluating the thickness of a surface layer of said stratified structure of said sample by using said frequency dependence curve for the propagation velocity.

2. Method for examining a surface of a sample by means of ultrasound according to claim 1, in which the evaluation of the thickness of the surface layer of said sample is effected by using frequencies corresponding to inflection points in said frequency dependence curve for the propagation velocity.

3. Method for examining a surface of a sample by means of ultrasound, comprising:
   a step of irradiating the sample through a liquid medium with a focused ultrasound beam;
   a step of repeating detection of ultrasound reflected by said sample while varying the frequency of said focused ultrasound beam in a predetermined frequency range;
   a step of storing detection output of the ultrasound reflected by said sample in memory means;
   a step of repeating said irradiation, detection and storage while varying the distance between said sample and the source of said focused ultrasound beam;
   a step of reading out successively the detection output stored in said memory means and obtaining curves representing variations of said detection output with respect to variations of said distance for each of the frequencies;
   a step of obtaining a frequency dependence curve for the propagation velocity of surface acoustic wave in said sample by measuring the propagation velocity on the basis of the period in said curves representing variations of detection output for each of the frequencies; and
   a step of evaluating the thickness of a layer having surface defects of said sample by using said frequency dependence curve for the propagation velocity.

4. Method for examining a surface of a sample by means of ultrasound according to claim 3, in which the evaluation of the thickness of the layer having surface defects of said sample is effected by using frequencies corresponding to inflection points in said frequency dependence curve for the propagation velocity.

* * * * *